United States Patent [19]

Caroleo

[11] Patent Number: 5,704,062
[45] Date of Patent: Jan. 6, 1998

[54] SUN VISOR

[76] Inventor: Rudolph Caroleo, 162-35 88th St., Jamaica, N.Y. 11414

[21] Appl. No.: 735,795

[22] Filed: Oct. 21, 1996

[51] Int. Cl.⁶ .................................................. A61F 9/00
[52] U.S. Cl. ................................. 2/12; 2/171; 2/209.3
[58] Field of Search ............................ 2/10, 11, 12, 15, 2/195.1, 171, 209.3

[56] References Cited

U.S. PATENT DOCUMENTS

| | | | |
|---|---|---|---|
| 1,532,317 | 4/1925 | Kingsbury | 2/12 |
| 3,582,991 | 6/1971 | Metz | 2/10 |
| 4,839,926 | 6/1989 | Choi | 2/10 |
| 4,955,087 | 9/1990 | Perez et al. | 2/12 |
| 5,347,655 | 9/1994 | Garrett | 2/10 |

*Primary Examiner*—Diana Biefeld
*Attorney, Agent, or Firm*—Michael I. Kroll

[57] ABSTRACT

A sun visor (10) comprising a headband (12) worn on a head (14) of a person (16). A bill (18) is provided, while a structure (20) is for pivotally connecting the bill (18) to the front of the headband (12). The bill (18) can be tilted to the left side, straight and then be tilted to the right side of the head (14) of the person (16), to block the rays (22) of the sun (24) that will normally shine into the eyes (26) of the person (16) and cause sun blindness.

16 Claims, 4 Drawing Sheets

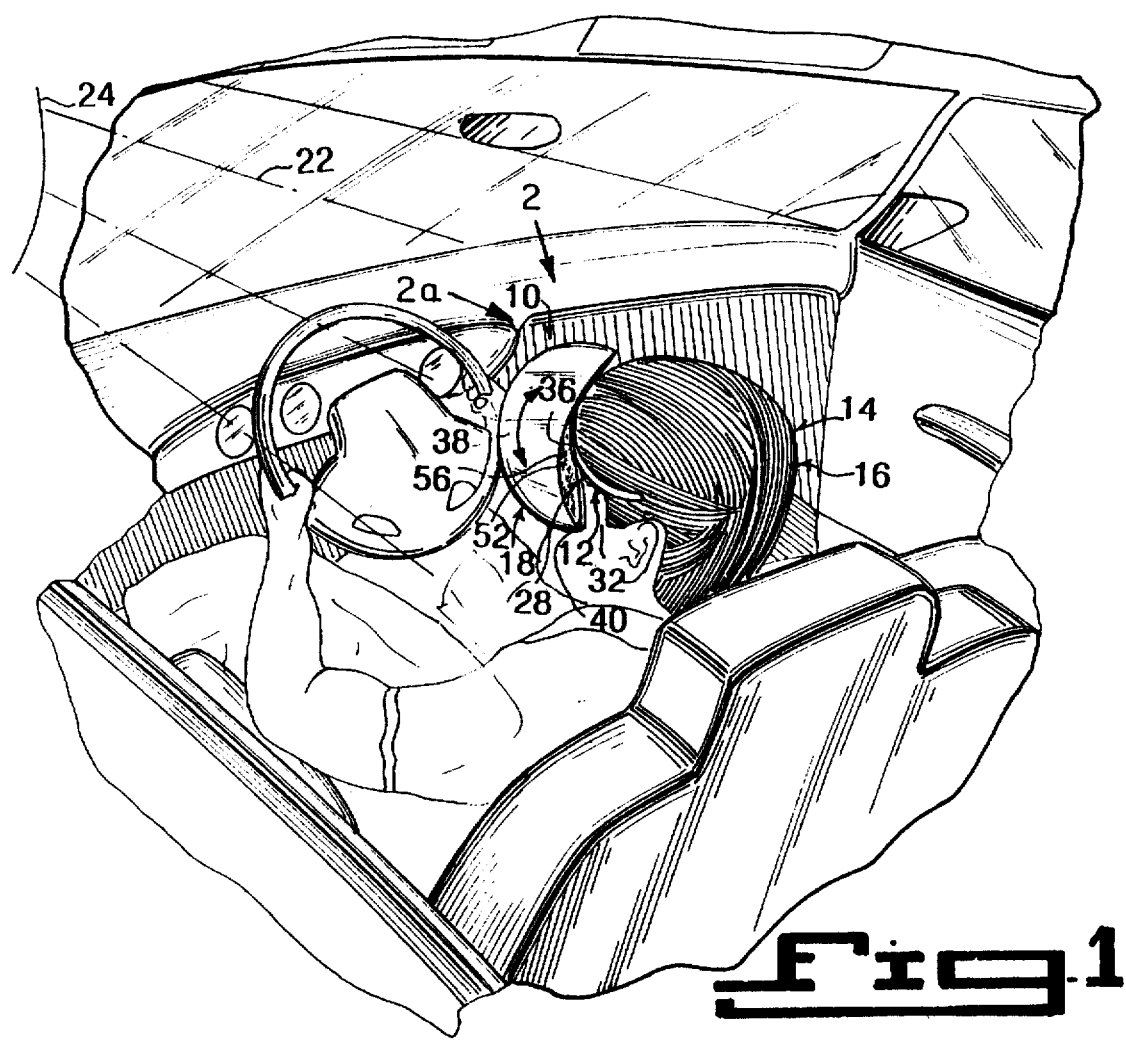
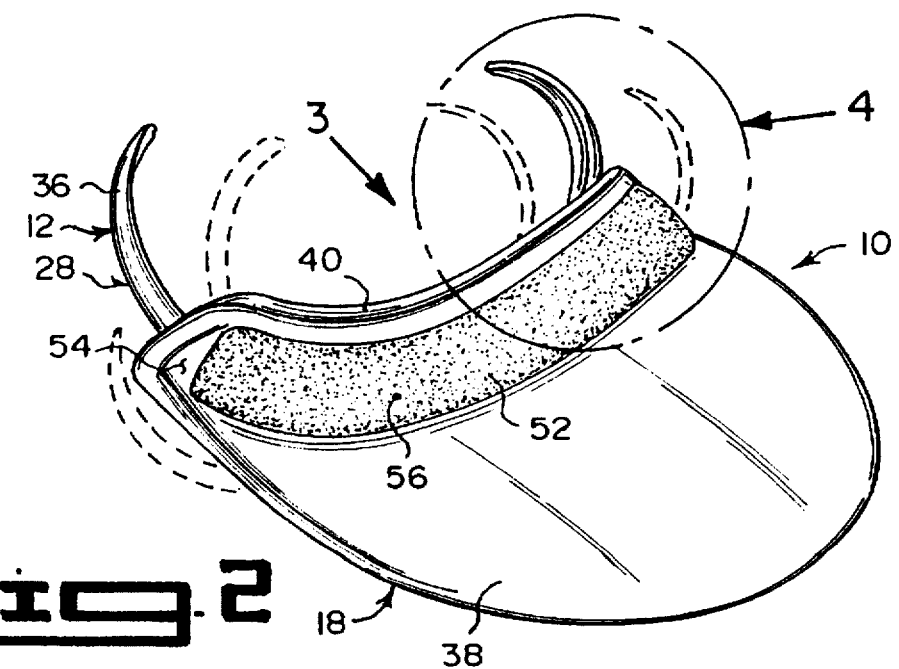

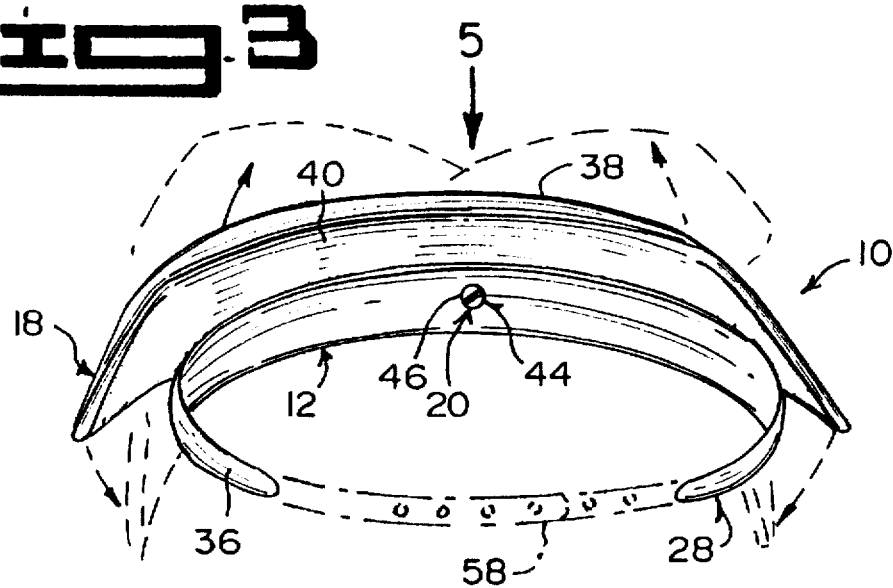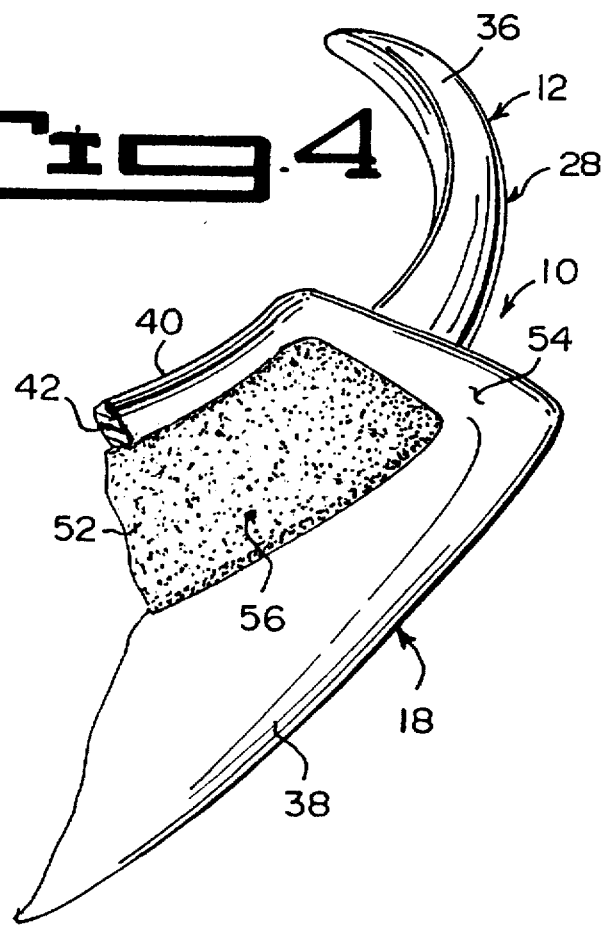

SUN VISOR

BACKGROUND OF THE INVENTION

1. Field of the Invention

The instant invention relates generally to headgear and more specifically it relates to a sun visor.

2. Description of the Prior Art

Numerous headgear have been provided in prior art. For example, U.S. Pat. Nos. 1,008,109 to Bickerton; 4,839,926 to Choi; 5,471,684 to Casale; 5,533,211 to Mehrens and 5,548,846 to Bianchetti all are illustrative of such prior art. While these units may be suitable for the particular purpose to which they address, they would not be as suitable for the purposes of the present invention as heretofore described.

BICKERTON, RICHARD F.

SUNSHADE

U.S. Pat. No. 1,008,109

A sunshade comprising a shade proper, and a wire frame having a cover frame to extend around the margin of the shade proper. A clasp is to encircle and engage upon a hat crown. A shank-like portion is integral with the clasp and connects the clasp with the cover frame. The shank-like portion is double-armed, whereby it can be contracted or expanded adjacent to its juncture with the clasp, to fit the clasp to hat crowns of different sizes. The terminals of the wire are twisted around the cover adjacent to the juncture thereof, with the shank extending from the clasp, all substantially as and for the purposes set forth.

CHOI, HAE Y.

CAP WITH BINOCULARS

U.S. Pat. No. 4,839,926

A cap with binoculars for using, both as a cap and binoculars, comprising a first member, a second member, pin means and binoculars.

CASALE, RUDY J.

CONVERTIBLE SPORTS CAP WITH SLIDING BRIM

U.S. Pat. No. 5,471,684

A sports hat construction includes a head covering portion having a lower opening defining a periphery. A brim portion is provided detachably secured to the head covering portion. An elongate band or strip, in the form of a male connector, is attached to the lower periphery of the head covering portion, while a female mating connector is secured to the brim. The male and female connectors are configurated and dimensioned to detachably engage each other in slidable relationship, so that the brim can be slidably moved along the longitudinal length of the periphery of the cap. Advantageously, the head covering portion is selectively removable to permit the brim to continue to serve as a sun visor when the head covering portion is removed.

MEHRENS, DOUGLAS W.

SLIDABLY REPOSITIONABLE HAT

U.S. Pat. No. 5,533,211

A hat having an attached accessory such as a visor is disclosed, incorporating a headband formed integrally with a sliding member positioned adjacent the opening the crown. A track is secured to the crown and slidingly engages the sliding member to permit the crown and attached visor to be rotated relative to the wearer's head without removing the hat.

BIANCHETTI, GEORGE

HEADWEAR WITH DETACHABLE BRIM

U.S. Pat. No. 5,548,846

This invention pertains to headwear equipped with a weather and environmental protection device insert that stores in a hidden fashion within the headwear, and instantly self expands upon removal and upon reattachment to the headwear exterior forms an effective protection unit to the head and body of the wearer. The protection device consists of one or more sphere shaped panels, each with a perimeter border of coilable spring wire formed in a loop, such loop covered with a variety of foldable protective fabric to form side or overhead panels. That these panels can deploy singly overhead to create a wide brim effect offering protection from sun and rain, or that such panels can also be joined together to create a tent-like protective framework about the head and body of the wearer. In either design, the protection device is easily coilable from its deployed broad cover by twist-fold pressure to form a small stack of concentric, over lapping spheres that fit comfortably and unobtrusively in the crown of the support headwear. The protective device is adaptable to a variety of standard off-the-shelf headwear as well as to designs that incorporate the headwear/protective device as one matching unit in a variety of fashion styles for men and women.

SUMMARY OF THE INVENTION

A primary object of the present invention is to provide a sun visor that will overcome the shortcomings of the prior art devices.

Another object is to provide a sun visor worn on a head of a person, that has a pivotable bill, which can be tilted to the left or right, to act as a shield and better block out the rays of the sun.

An additional object is to provide a sun visor that will prevent the rays of the sun coming from the left side or right side to shine into the eyes of a person, especially when that person is driving a motor vehicle, so as to eliminate sun blindness and reduce the chance of an accident.

A further object is to provide a sun visor that is simple and easy to use.

A still further object is to provide a sun visor that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in

3 conjunction with the accompanying drawings, in which like reference characters designate the same or similar parts throughout the several views, and wherein;

FIG. 1 is a side perspective view of the instant invention worn on a head of a person being used in a motor vehicle.

FIG. 2 is a front perspective view of the instant invention per se taken in the direction of arrow 2 in FIG. 1.

FIG. 3 is a rear perspective view taken in the direction of arrow 3 in FIG. 2.

FIG. 4 is an enlarged front perspective view of the area indicated by arrow 4 in FIG. 2.

Similar reference characters denote corresponding features consistently throughout the attached drawings.

DETAILED DESCRIPTION OF THE PREFERRED EMBODIMENTS

Figure 2A:
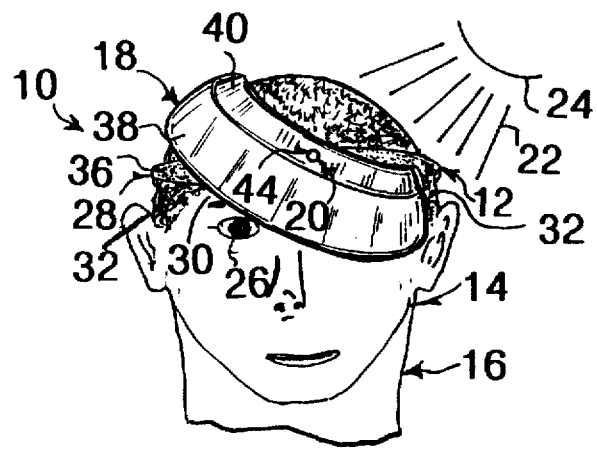
FIG. 2a is a front view taken in the direction of arrow 2a in FIG. 1, showing the bill tilted to the left.
Figure 2B:
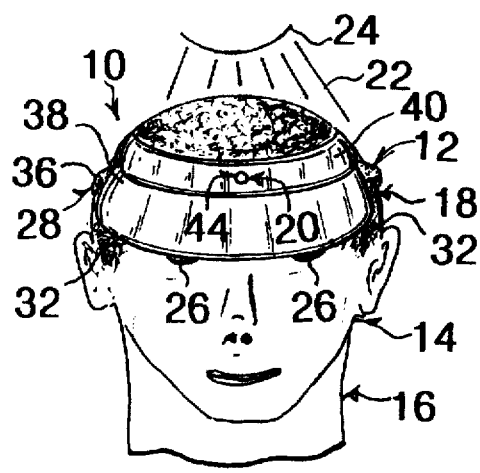
FIG. 2b is a front view similar to FIG. 2a, showing the bill straight.
Figure 2C:
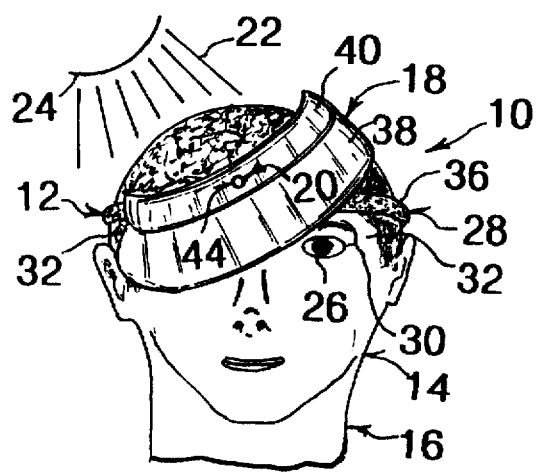
FIG. 2c is a front view similar to FIG. 2a, showing the bill tilted to the right.
Figure 5:
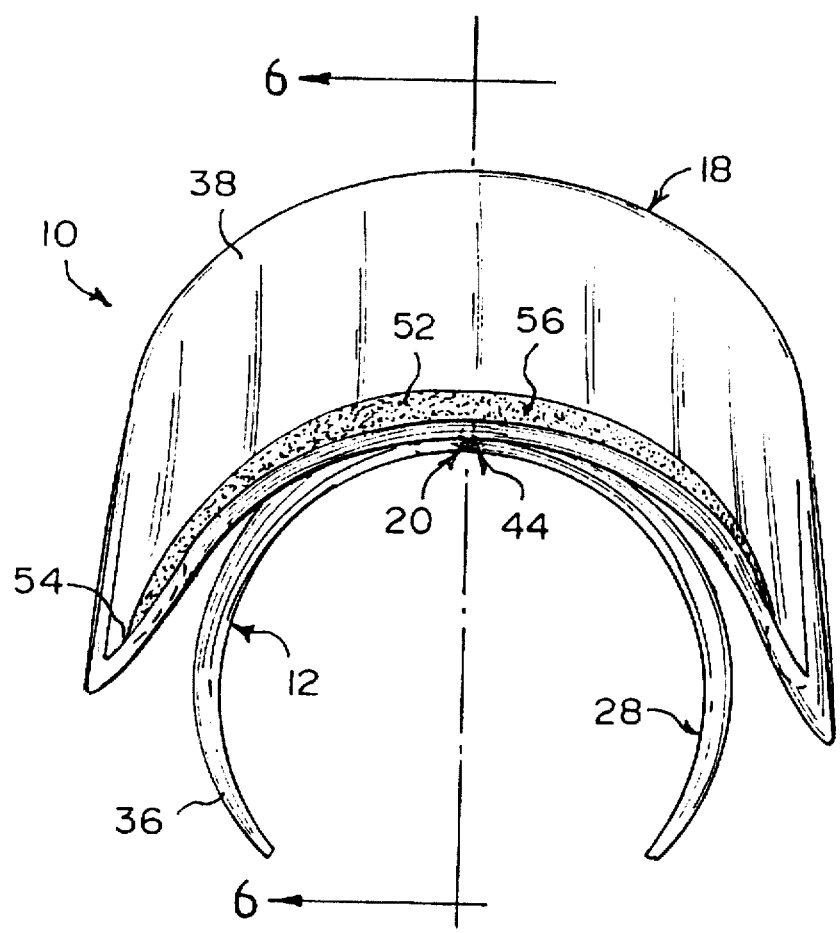
FIG. 5 is a top view taken in the direction of arrow 5 in FIG. 3.

Turning now descriptively to the drawings, in which similar reference characters denote similar elements throughout the several views, FIGS. 1 to 6 illustrate a sun visor 10 comprising a headband 12 worn on a head 14 of a person 16. A bill 18 is provided, while a structure 20 is for pivotally connecting the bill 18 to the front of the headband 12. The bill 18 can be tilted to the left side, straight and then be tilted to the right side of the head 14 of the person 16, to block the rays 22 of the sun 24 that will normally shine into the eyes 26 of the person 16 and cause sun blindness.

The headband 12 is a flexible strip 28, which fits against a forehead 30 and temples 32 on the head 14 of the person 16. The headband 12 is fabricated out of a plastic material 34. The headband 12 further includes padded material 36 thereabout, to provide comfort when worn against the forehead 30 and temples 32 on the head 14 of the person 16. The bill 18 consists of a peak portion 38 and an upstanding portion 40, integrally formed to the peak portion 38. The bill 18 is fabricated out of a plastic material 42.

Figure 6:
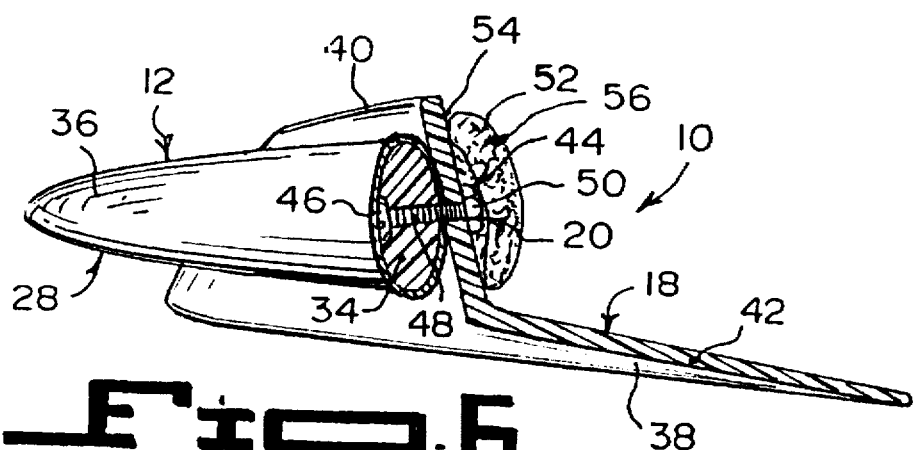
FIG. 6 is an enlarged cross sectional view taken along line 6—6 in FIG. 5.

The pivotally connecting structure 20 is a fastener assembly 44. The fastener assembly 44, as best seen in FIG. 6, comprises a bolt 46 having a threaded shaft 48 which extends through the center of the upstanding portion 40 of the bill 18 and the front of the headband 12. A nut 50 threads onto a free end of the threaded shaft 48 of the bolt 46.

The sun visor 10 can further include a decorative strap 52 affixed to a front surface 54 of the upstanding portion 40 of the bill 18, so as to hide the pivotally connecting structure 20 and enhance the appearance of the sun visor 10. The decorative strap 52 is fabricated out of a fabric material 56. The decorative strap 52 can be affixed to the front surface 54 of the upstanding portion 40 by adhesive or other types of attaching members (not shown).

A flexible adjustable connector 58, shown in phantom in FIG. 3, can extend between distal free ends of the headband 12. The flexible adjustable connector 58 will allow the headband 12 to snugly fit onto the head 14 of the person 16. The headband 12, the bill 18 and the decorative strap 52 can come in many different coordinated or matching colors, to please the person 16 wearing the sun visor 10. The headband 12 and the bill 18 can also be fabricated out of other durable materials, so as not to limit the sun visor 10 to materials described above or illustrated in the drawings.

Operation of the Invention

To use the sun visor 10, the following steps should be taken:

1. Place the headband 12 against the forehead 30 and temples 32 on the head 14 of the person 16 on a sunny day.
2. Adjust the adjustable connector 58, if being used, so that the headband 12 will snugly fit onto the head 14 of the person 16.
3. Tilt the bill 18 to the left side to block the rays 22 of the sun 24 when coming from the left, so as not to shine into the eyes 26 of the person 16 (see FIG. 2a).
4. Tilt the bill 18 to the right side to block the rays 22 of the sun 24 when coming from the right, so as not to shine into the eyes 26 of the person 16 (see FIG. 2c).
5. Keep the bill 18 straight to block the rays 22 of the sun 24 when coming from directly above, so as not to shine into the eyes 26 of the person 16 (see FIG. 2b).
6. Remove the headband 12 from the forehead 30 and temples 32 on the head 14 of the person 16, on a cloudy day or at night when the sun 24 is not shining.

List of Reference Numbers

| | |
|---|---|
| 10 | sun visor |
| 12 | headband of 10 |
| 14 | head of 16 |
| 16 | person |
| 18 | bill of 10 |
| 20 | pivotally connecting structure of 10 |
| 22 | rays of 24 |
| 24 | the sun |
| 26 | eye of 16 |
| 28 | flexible strip for 12 |
| 30 | forehead on 14 |
| 32 | temple on 14 |
| 34 | plastic material of 12 |
| 36 | padded material on 12 |
| 38 | peak portion of 18 |
| 40 | upstanding portion of 18 |
| 42 | plastic material of 18 |
| 44 | fastener assembly for 20 |
| 46 | bolt of 44 |
| 48 | threaded shaft of 46 |
| 50 | nut of 44 |
| 52 | decorative strap of 10 |
| 54 | front surface on 40 |
| 56 | fabric material for 52 |
| 58 | flexible adjustable connector |

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A sun visor comprising:
   a) a headband worn on a head of a person;
   b) a bill having a peak portion and an upstanding portion integrally formed to said peak portion;
   c) means for pivotally connecting said bill to a front of said headband; and
   d) a decorative strap affixed to a front surface of said upstanding portion of said bill, so as to hide said pivotally connecting means and enhance the appearance of said sun visor.

2. A sun visor as recited in claim 1, wherein said headband is a flexible strip which fits against a forehead and temples on the head of a person.

3. A sun visor as recited in claim 2, wherein said headband is fabricated out of a plastic material.

4. A sun visor as recited in claim 3, wherein said headband further includes padded material, to provide comfort when worn against the forehead and temples on the head of a person.

5. A sun visor as recited in claim 4, wherein said bill is fabricated out of a plastic material.

6. A sun visor as recited in claim 5, wherein said pivotally connecting means is a fastener assembly.

7. A sun visor as recited in claim 6, wherein said fastener assembly includes:
   a) a bolt having a threaded shaft which extends through a center of said upstanding portion of said bill and a front of said headband; and
   b) a nut that threads onto a free end of said threaded shaft of said bolt.

8. A sun visor as recited in claim 7, wherein said decorative strap is fabricated out of a fabric material.

9. A sun visor as recited in claim 8, further including a flexible adjustable connector extending between distal free ends of said headband, so that said flexible adjustable connector will allow said headband to snugly fit onto the head of the person.

10. A sun visor as recited in claim 1, wherein said headband is fabricated out of a plastic material.

11. A sun visor as recited in claim 1, wherein said headband further includes padded material, to provide comfort when worn against the forehead and temples on the head of a person.

12. A sun visor as recited in claim 1, wherein said bill is fabricated out of a plastic material.

13. A sun visor as recited in claim 1, wherein said pivotally connecting means is a fastener assembly.

14. A sun visor as recited in claim 13, wherein said fastener assembly includes:
   a) a bolt having a threaded shaft which extends through a center of said upstanding portion of said bill and a front of said headband; and
   b) a nut that threads onto a free end of said threaded shaft of said bolt.

15. A sun visor as recited in claim 1, wherein said decorative strap is fabricated out of a fabric material.

16. A sun visor as recited in claim 1, further including a flexible adjustable connector extending between distal free ends of said headband, so that said flexible adjustable connector will allow said headband to snugly fit onto the head of a person.

* * * * *